United States Patent
Ranganathan et al.

(10) Patent No.: US 7,942,825 B2
(45) Date of Patent: May 17, 2011

(54) METHOD AND DEVICE FOR MONITORING THERMAL STRESS

(75) Inventors: Sridhar Ranganathan, Suwanee, GA (US); Andrew Thomas Baker, Norcross, GA (US); Ralph Andrew Solarski, Alpharetta, GA (US); Joel P. Anderson, Appleton, WI (US); Jeanne Marie Gatto, Alpharetta, GA (US); Jeff Heller, Neenah, WI (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 527 days.

(21) Appl. No.: 12/135,686

(22) Filed: Jun. 9, 2008

(65) Prior Publication Data
US 2009/0306536 A1 Dec. 10, 2009

(51) Int. Cl.
| | |
|---|---|
| A61B 5/00 | (2006.01) |
| G01K 17/00 | (2006.01) |
| G01K 3/00 | (2006.01) |
| G01K 1/02 | (2006.01) |
| G01K 5/70 | (2006.01) |
| G01K 5/00 | (2006.01) |
| G01K 9/00 | (2006.01) |

(52) U.S. Cl. .......... 600/549; 374/29; 374/107; 374/186; 374/204; 374/205
(58) Field of Classification Search .............. 600/549; 374/29–30, 100–102, 107, 186, 204, 205
See application file for complete search history.

(56) References Cited

U.S. PATENT DOCUMENTS

| | | | |
|---|---|---|---|
| 4,090,504 | A | 5/1978 | Nathan |
| 4,129,125 | A | 12/1978 | Lester et al. |
| 4,312,358 | A | 1/1982 | Barney |
| 4,509,531 | A | 4/1985 | Ward |
| 4,595,020 | A | 6/1986 | Palti |
| 4,679,566 | A | 7/1987 | Tamm |
| 4,883,063 | A | 11/1989 | Bernard et al. |
| 5,062,432 | A | 11/1991 | James et al. |
| 5,938,619 | A | 8/1999 | Dogre Cuevas |
| 6,056,435 | A | 5/2000 | Pompei |
| 6,198,394 | B1 | 3/2001 | Jacobsen et al. |
| 6,199,550 | B1 | 3/2001 | Wiesmann et al. |

(Continued)

FOREIGN PATENT DOCUMENTS
KR 10-2005-0063781 A 6/2005
(Continued)

OTHER PUBLICATIONS

Doherty, T.J. et al., "Evaluation of the Physiological Bases of Thermal Comfort Models," Center for the Built Environment, University of California, Berkeley, ASHRAE Transactions, vol. 94, Part 1, 1988, pp. 1371-1385.

(Continued)

*Primary Examiner* — Max Hindenburg
*Assistant Examiner* — John Pani
(74) *Attorney, Agent, or Firm* — Nancy M. Klembus; Nathan P. Hendon

(57) ABSTRACT

A method and device for monitoring thermal stress in a user is described. The device is designed to include a material having specific thermodynamic properties and physical dimensions defined as a function of those thermodynamic properties. A system for thermal stress monitoring including a thermal stress monitoring device configured within a garment is also described.

24 Claims, 11 Drawing Sheets

U.S. PATENT DOCUMENTS

| | | |
|---|---|---|
| 6,257,759 B1 | 7/2001 | Witonsky et al. |
| 6,292,685 B1 | 9/2001 | Pompei |
| 6,491,037 B1 | 12/2002 | Mortenson |
| 6,491,647 B1 | 12/2002 | Bridger et al. |
| 6,579,231 B1 | 6/2003 | Phipps |
| 6,852,085 B2 | 2/2005 | Rubinstein |
| 6,995,665 B2 | 2/2006 | Appelt et al. |
| 7,020,508 B2 | 3/2006 | Stivoric et al. |
| 7,187,960 B2 | 3/2007 | Abreu |
| 7,298,535 B2 | 11/2007 | Kuutti |
| 2005/0043631 A1 | 2/2005 | Fraden |
| 2005/0245839 A1 | 11/2005 | Stivoric et al. |
| 2006/0224077 A1 | 10/2006 | Pauly et al. |
| 2007/0177651 A1 | 8/2007 | Daugherty et al. |
| 2007/0206655 A1 | 9/2007 | Haslett et al. |
| 2007/0239038 A1 | 10/2007 | Nicolaescu et al. |
| 2007/0295713 A1 | 12/2007 | Carlton-Foss |
| 2009/0198112 A1 | 8/2009 | Park et al. |
| 2010/0121217 A1* | 5/2010 | Padiy et al. ............... 600/549 |

FOREIGN PATENT DOCUMENTS

| | | |
|---|---|---|
| KR | 10-2007-0060968 A | 6/2007 |

OTHER PUBLICATIONS

Freitas, Jr., R.A., "Table 8.12 Thermophysical Characteristics of Various Body Tissues, Organs, and Other Materials," 1999, http://www.nanomedicine.com/NMI/Tables/8.12.jpg, viewed and printed Jul. 16, 2008.

Herman, I.P., Tables 1.3 and Tables 6.36, *Physics of the Human Body*, Springer, Berlin, 2007, pp. 16 and 362.

Low, D.A. et al., "Temporal Thermometry Fails to Track Body Core Temperature During Heat Stress," Medscape, www.medscape.com, 2007, 5 pages.

Parsons, K., Table 14.3, *Human Thermal Environments*, Taylor & Frances, London, 1993, p. 397.

* cited by examiner

METHOD AND DEVICE FOR MONITORING THERMAL STRESS

BACKGROUND

Under normal circumstances the human body is exceptionally efficient at regulating a constant internal temperature. However, increased workload compounded by environmental factors such as air temperature, radiant heat sources, and humidity may stress the body's ability to safely regulate its internal temperature. Heat stress is a potentially dangerous build up of heat within a body and is a hazard faced by many workers and athletes. The use of necessary protective apparel when working in hot environments puts such workers at an increased risk of heat stress. On the other end of the temperature spectrum, workers in cold environments are at risk of an unsafe decrease in the body core temperature known as hypothermia.

The current industry practice to limit the potential hazard of thermal stress includes controlling work/rest cycles based on environmental conditions. Such guidelines are conservative estimates based on average workers and vary based on a person's age, weight, physical fitness, degree of acclamation, use of alcohol or drugs, various medical conditions, clothing being worn, and other individual-specific factors. Thermal stress, both heat stress and hypothermia, is indicated by several physiological changes and has been studied extensively in the past. Many thermal stress indicators involve consideration of the environmental factors and individual-specific factors as discussed above and comparing them with known tabulated data. However, such measurements and use of reference materials is not necessarily convenient or practical in the average dynamic work environment.

One key indicator for determining the onset of thermal stress (either heat stress or hypothermia) is the true core body temperature. Multiple safety standards agree that the body core temperature should not be allowed to exceed 38° C. for extended periods of time, nor should the core temperature be allowed to increase at a rate of much greater than 1° C. per hour. Similarly, the onset of hypothermia occurs when the body core temperature drops below 35° C.

There are several known methods to measure/estimate core temperature. Invasive techniques used include rectal probes, esophageal catheters or capsules that are swallowed. When patients are catheterized, blood temperature or urine temperature in the bladder may also be used as a good indicator of core body temperature. While such invasive measurement methods work well for patients in a controlled environment, such techniques are not feasible for use with workers in a comparatively uncontrolled working environment or for an athlete undertaking their particular activity. Such invasive methods are even less practical in situations where continuous monitoring the core temperature of such a worker or athlete is desired.

Several minimally invasive methods of estimating the core body temperature from skin temperature measurements have been developed. Due to the differences between the skin temperature and the core body temperature, such methods have to modify the measured skin temperature to estimate the true body core temperature. Some such estimates modify the measured skin temperature utilizing other environmental data such as ambient temperature and ambient humidity, either measured by the device or inputted by the user. Other estimates of core body temperature require input or acquisition of user-specific data. For example, a series of baseline measurements may be taken over a period of time to calibrate the skin temperature measurements for the particular user. Other such estimates are left in insulated contact with the skin of the user until a presumed equilibrium of body core temperature and skin temperature is reached in the region of insulated contact. All of such estimates of body core temperature are often adequate for monitoring the temperature of a patient in the controlled care environment.

However, such estimates of core temperature are user-specific and are not practical for the working environs, and under the conditions, in which a worker or athlete may be at risk for thermal stress and would particularly benefit from such monitoring. For example, as a worker (or athlete) exerts himself or herself, their body temperature may rapidly increase. Their body will attempt to regulate the internal body temperature through various methods including increasing perspiration for the purposes of evaporative cooling. In such situations of rapid temperature change and cooling of the skin by perspiration, the assumptions underlying existing models of estimating core temperature from skin temperature are broken. Thus, estimates of core body temperature may become more inaccurate in situations of rapid temperature change and increased subject perspiration; the very situations in which such thermal stress monitoring is most needed.

Definitions

As used herein, the term "thermal stress" refers to a state in which the internal core temperature of a body is outside of the safe operating temperature range. Thermal stress includes states of excessive internal core temperature (i.e., hyperthermia or heat stress) and states of unsafe reduced internal core temperature (i.e., hypothermia).

As used herein, the term "non-invasive" refers to not entering the skin or a body cavity. Non-invasive monitoring involves monitoring that does not include entering the skin, insertion into a body orifice (e.g., insertion into ear, rectum, or other orifice), or otherwise entering a body cavity (e.g., such as by ingestion). "Entering the skin" as used herein, refers to penetrating the skin to a deep enough level to leave a wound or other damage, i.e., typically referring to penetration deeper than the stratum corneum level of the skin.

As used herein, the term "disposable" is not limited to single use articles but also refers to articles that are so relatively inexpensive to the consumer that they can be discarded if they become soiled or otherwise unusable after only one or a few uses.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates or materials added to enhance ability to process a composition.

As used herein, the term "couple" or "affix" includes, but is not limited to, joining, connecting, fastening, linking, or associating two things integrally or interstitially together. As used herein, the term "releaseably affix(ed)" refers to two or more things that are stably coupled together and are at the same time capable of being manipulated to uncouple the things from each another.

As used herein, the term "configure" or "configuration" means to design, arrange, set up, or shape with a view to specific applications or uses. For example: a military vehicle that was configured for rough terrain; configured the computer by setting the system's parameters.

As used herein, the term "substantially" refers to something which is done to a great extent or degree; for example, "substantially covered" means that a thing is at least 95% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the terms "thermal conductance" or "conductance" refers to the ratio of thermal conductivity of a layer to its thickness.

SUMMARY OF THE INVENTION

In light of the problems discussed above, the inventors have tested the assumptions underlying the simple thermal models used by common temperature monitors to estimate body core temperature from skin temperature. They have found that these models fail to adequately account for the dynamic conditions experienced by persons at increased risk for thermal stress. Specifically, such models fail to account for rapid temperature change, the effects of evaporative cooling due to perspiration, and fail to design devices with the materials and dimensions necessary to reduce errors in temperature estimates that such factors may influence.

The present disclosure is directed to a method for more accurately estimating the core body temperature and aiding a user to prevent thermal stress. The method includes a first step of providing a device having at least one first temperature sensor, at least one second temperature sensor, and an insulating layer between the first and second sensors. Further, the insulating layer is designed to have a defined thermal conductance and the temperature sensor is placed no closer to the peripheral edge of the insulating layer than a distance which is a function of the insulating layer's thermal conductance. The method further includes the steps of placing the device in thermal contact with the skin of the user, determining the heat flux from the skin through the device, and finally determining the body core temperature and change in body core temperature as a function of heat flux.

In various optional embodiments of the method, the method may include steps of proving an alert when the determined core temperature is outside a threshold core temperature range, and/or providing an alert when the determined change in core temperature is outside a threshold change in core temperature range.

The present disclosure is also directed to a non-invasive device estimating the core temperature and aiding a user to prevent thermal stress. The device includes at least one first temperature sensor, at least one second temperature sensor, and an insulating layer between the first and second sensors. Further, the insulating layer is designed to have a defined thermal conductance and the temperature sensor is placed no closer to the peripheral edge of the insulating layer than a distance which is a function of the insulating layer's thermal conductance. In further optional embodiments, the device may include a processor, stored alert ranges, stored warning ranges, and/or an alert mechanism.

Finally, the present disclosure is also directed to a system for continuous monitoring the thermal stress of a user. The system includes a thermal stress monitoring device and a garment that places the monitoring device in thermal communication with the skin of the user. In various embodiments, the garment of the system may include a bandage, a sweatband, a hardhat, a welding helmet, a hood, eyewear, a cap, or other items that may be worn by a user. In various embodiments, the system may further include an alert mechanism, an alarm reset, and/or a proximity sensor.

DETAILED DESCRIPTION

Figure 1:
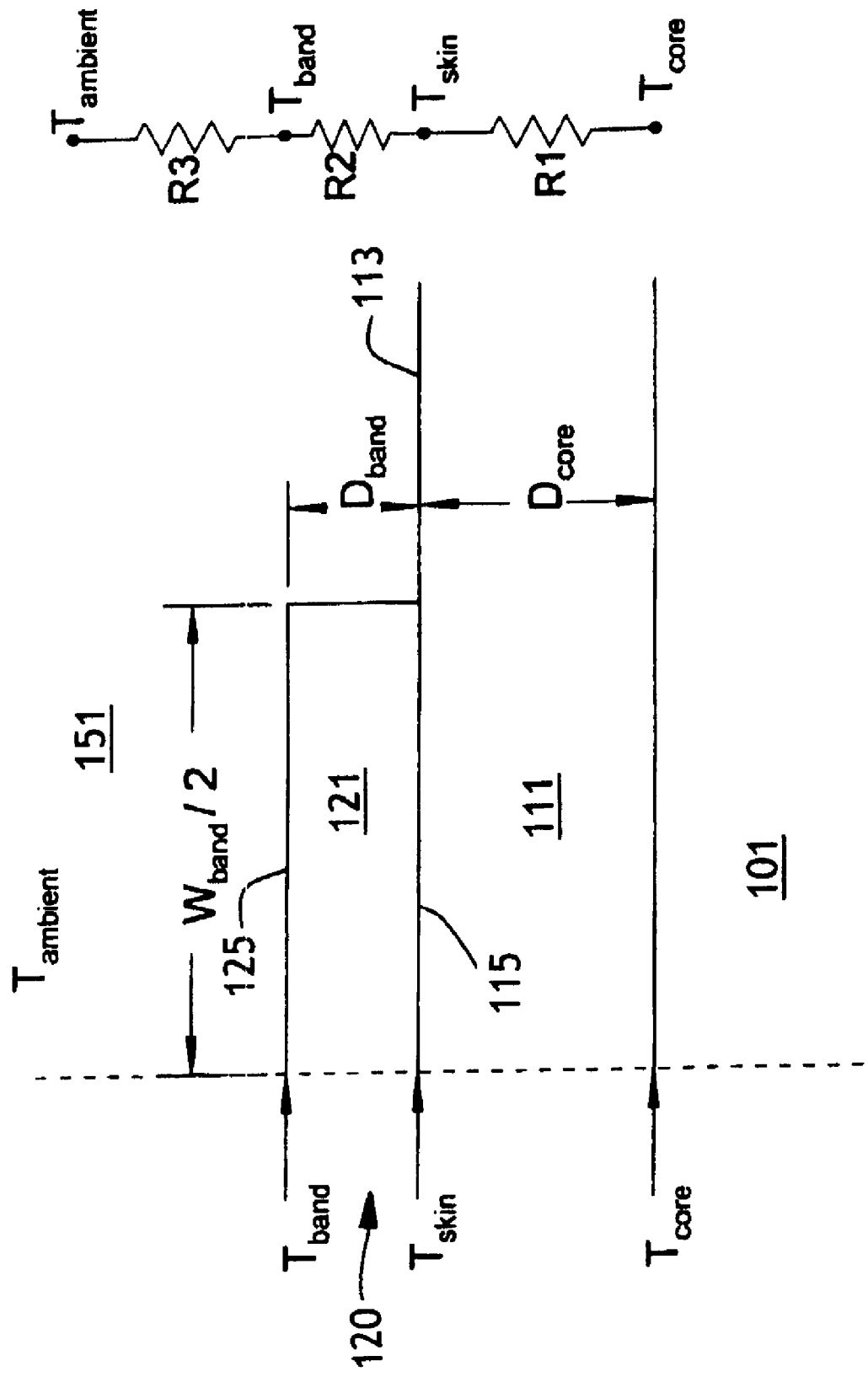
FIG. 1 illustrates a one-dimensional heat balance model used for determining parameters for thermal stress monitoring in accordance with devices of the prior art.

The present invention pertains to a method for non-invasive monitoring of thermal stress in a user and a device used in providing such monitoring. The user may use such a device while in environments they wish to work in, engage in athletic activities, or otherwise be present. Such a device and method of monitoring may be especially useful in environments and conditions where a user may be at higher risk for thermal stress. The materials and configuration of the device, and its method of use, are uniquely designed to more accurately account for the conditions in which thermal stress may be a danger. For example, such a device may be useful in helping a firefighter monitor themselves for heat stress when fighting a blaze while wearing full-protective gear. Similarly, such a device may be useful in helping athletes to monitor themselves for heat stress while exerting themselves on a hot and humid day. Such a device may help a commercial fisherman in the cold and wet environment to monitor themselves for the onset of hypothermia. Likewise, such a device may help any workers to monitor themselves for thermal stress in the particular environment in which they must work.

While it is preferred that such a thermal stress monitoring device be reusable, it is also contemplated that the device may be disposable.

The human body has an internal core temperature that is kept within a relatively small temperature range for the systems of the body to function properly. Thermal stress from the internal core temperature being too high (i.e., hyperthermia or heat stress) or the internal core temperature being too low (i.e., hypothermia) can result in the failure of various systems of the body and may ultimately result in death. It is intended that both extremes of thermal stress may be monitored by the device of the present disclosure. As heat stress is the more common concern in the majority of work environments, and for the sake of simplicity, the bulk of the discussion herein will be directed to heat stress. However, the models and devices discussed herein with regard to heat stress would likewise apply for hypothermia.

As discussed above, existing devices generally estimate the internal core temperature, using a variety of physiological measures, including skin temperature. The human body has an interior core temperature that is maintained within a fairly narrow window irrespective of the skin temperature and tissue temperature close to the skin for organs to function properly. The core compartment of the body extends to within various distances from the skin in different locations. In some places it is several centimeters below the surface skin while in some other locations it could be within a few millimeters below the surface of the skin.

A known method to estimate core temperature is to measure the skin temperature and estimated skin heat flux to infer the core temperature. One such approach is used in commercially available forehead thermometers. The instantaneous value of the maximum skin temperature as measured by scanning the forehead, along with ambient temperature, is used in the core temperature estimate. This is suitable only for discrete measurements. For continuous monitoring of core temperature wearable patches have been proposed. One such approach is to have an insulating material so that the skin temperature becomes a good estimate of the core temperature. Another approach is to use an insulating material of known thermal conductivity and thickness as the wearable patch while measuring skin temperature underneath the patch and at another location away from the skin separated by the insulating material. Measuring the two temperatures permits the calculation of heat flux across the insulating material.

Existing devices estimate core body temperature by assuming the heat flux leaving the body core is equivalent to the flux leaving the skin surface. This is a reasonable approach when applied to the whole body after it has reached a thermal steady state condition thermally. When the assumption that the body temperature is at a steady state with the environment and for the cases where the heat flux leaving the skin is the same everywhere on the skin surface, it is possible to use a one-dimensional model of heat flux to characterize the core body temperature (see FIG. 1). The resulting equation is straightforward and is readily calculated by relatively simple inexpensive electronic circuits.

The requirement of the body being at steady state is in apparent conflict with the desire to develop a device that accurately tracks the core body temperature as it changes in response to the wearers activity and surrounding environment. The magnitude of the error that is caused when the steady state condition is invalid depends on multiple factors. In the case that the heat capacity of the device is relatively low and its thermal conductivity is high the difference between the dynamic and the steady state cases is negligible. Devices designed to track dynamic changes in core body temperature are therefore constrained to specific thermal properties if they are to provide an accurate estimate of core temperature.

The assumption that heat flux is uniform at all locations in the skin is markedly inaccurate. It is possible to apply the one-dimensional approach to a more localized portion of the body when the estimation of a local internal temperature is desired. This is the case, for example, with devices designed to measure the temperature of blood moving in vessel(s) near the surface of the skin. Measurements of blood temperature in temporal and femoral arteries have been used as estimates of core body temperature. This more localized approach to the one-dimensional heat flow model is reasonable when the local heat flux can be measured accurately. The local heat flux can be altered significantly by the devices designed to measure it. The impact of the measuring device on the local heat flux is arguably the most significant factor impacting the validity of the use of a one-dimensional heat flux model when estimating core temperature.

The one-dimensional heat flux approach is accurate on a localized scale when the heat flux measured by the device is essentially the same as the flux leaving the localized area; heat moving through the device is the same as heat moving through the body. When the device is highly insulative, a portion of the heat leaving the body will move around the device and the measured flux through the device is reduced correspondingly. Some have recognized that the higher the insulation of the device the smaller the difference between the skin and core temperatures and have suggested this as a method to estimate core temperature. This approach assumes the heat flux around the device can be ignored. While there are specific cases where this is a valid assumption it is in general incorrect and in the case of evaporative heat loss the error can be quite significant.

It should be noted that this assumption of existing heat stress monitoring and measuring devices that utilize such a simplified one-dimensional model is often appropriate and accurate enough for the common usage of such monitors and measuring devices. For example, in situations where a patient is being cared for in a hospital, the patient is in an optimally controlled environment (i.e., controlled ambient temperature and humidity). Also, such patients are normally not undergoing any physical activity that may otherwise raise their body temperature. Thus, the environment and patient are allowed to reach a pseudo-equilibrium state. Additionally evaporative loss from the skin is minimal when subjects are inactive as is the case for most hospital patients.

Under such optimum conditions, the environmental conditions and the internal body temperature of the patient is generally not prone to increasing at the rate that may be experienced by a worker or athlete dramatically increasing their activity in an uncontrolled environment. Thus, the one-dimensional approach may provide adequate accuracy to devices used for monitoring and estimating core temperature, via skin temperature measurements in the static environments (i.e., hospitals) in which such devices are intended to be used. However, the inventors have found that in the critical situations where measurement of thermal stress is most needed for workers and athletes (i.e., high heat and humidity work environments with increased physical exertion by the worker/athlete) other factors affect the accuracy of the one-dimensional model. The obvious concern is that the one-dimensional approach becomes more inaccurate at the time and circumstances when accuracy is most critical. Therefore, while expressions for core temperature estimation from skin temperature and another temperature to estimate heat flux have been discussed previously for existing heat stress monitors and measuring devices, there has been no recognition of the critical role other factors play in controlling the overall error in core temperature estimates.

The factors affecting the heat flux around the measuring device are many. The thermal conductivity of the device, its overall area on the skin, and the amount of evaporation occurring on the skin are considered to be the most significant. As discussed earlier a high thermal conductivity makes the device more responsive in time, it also reduces the fraction of heat moving around the device. High conductivity reduces the temperature drop across the insulative layer requiring thermal sensors with higher accuracy to maintain equal device accuracy. Designing a device to have an appropriate time responsiveness and temperature accuracy requires considering the thermal sensor accuracy and selecting material thermal conductivity balancing the requirements of time responsiveness with device accuracy.

A "standard man" (see Herman. I. P., Physics of the Human Body, Springer, Berlin, 2007, p. 16) produces about 44 W/m$^2$ of heat when at rest. A heat stress indicator device with high thermal conductivity would have a surface temperature similar to the skin and would have a similar heat loss through the device. A less conductive device would have smaller heat flux through the device. A practical upper range of sweat production for an adult is one liter per hour (see Parsons. K., Human Thermal Environments, Taylor & Frances, London, 1993, p. 397). If this amount of sweat were to evaporate from a person with two square meters of skin surface area, approximately 400 Watts of heat loss would occur per square meter of skin. This additional heat loss does not occur on the surface of the device because it doesn't sweat. If this amount of heat loss were occurring at the skin surface adjacent to the heat stress indicator device then heat flux around the product would be substantial. A device that uses a simple one-dimensional heat flux approximation would substantially over estimate the core body temperature because the measured flux was low but the actual heat loss from the entire body was much higher. A device that could accurately measure heat flux around the device may be able to account for this loss. Alternately, a device with sufficient surface area on the skin would minimize the impact of evaporative losses.

A device that is large enough that the evaporative heat loss is no longer part of the local environment would minimize its impact on measuring local heat flux. Quantifying what constitutes 'large enough' requires calculations that account for heat loss both around and through the heat stress indicator device.

Therefore in order to minimize the error estimating core temperature using the one-dimensional heat flow model the device conductance must be large enough to prevent significant heat loss around the product and the corresponding error in heat flux measurement and yet have low enough conductance that the temperature drop across the insulation layer is large with respect to the error in the temperature sensors. The optimum design balances these opposing design criteria.

While in principle it would be possible to select an appropriate insulation material, its thickness, and overall dimensions as well as the temperature sensor accuracy by trial and error, such an undertaking is impractical and extraordinarily costly primarily because of the exceptionally large number of options available for nearly all aspects of the design. The design constraints provided in this present invention allow the designer to efficiently develop device specifications.

The heat stress monitoring device measures the heat flux leaving the body by measuring the temperature drop across a known thermal insulator. The device performance quality depends on balancing two factors. Temperature drop across the device must be large compared to the error in the temperature sensors. This puts constraints on the thermal conductance of the insulating layer. In addition, the heat flux through the device must be much larger than the heat flux moving around the device. This puts constraints on the product size.

These design constraints can be characterized by equations describing the physical or statistical phenomena. FIG. 1 illustrates a model of the one-dimensional thermal balance. The one-dimensional steady state equation for core body temperature is given by equation (1).

$$T_{core} = T_{skin} + \frac{L_{band}}{L_{core}}(T_{skin} - T_{band}) \tag{1}$$

Where $T_{skin}$ is the temperature of the skin under the sensing device, $T_{band}$ is the temperature measure on top 125 of the thermal insulating layer 121 of the device 120. $L_{band}$ is the thermal conductance of the insulating layer 121 or the ratio of the thermal conductivity to the layer thickness. Correspondingly, $L_{core}$ is the thermal conductance of the body.

The movement of heat is analogous to the movement of electricity in a circuit. The series of resistors R1, R2, and R3 shown on the right side of FIG. 1 represent the one-dimensional heat movement through the various layers described on the left side of FIG. 1. Current flow in the electrical circuit is analogous to heat flow (Joules/second or Watts). The resistance in the circuit is analogous to the inverse of conductance. Just as a voltage drop across a finite resistance causes electricity to flow, temperature drop across a finite thermal resistance causes heat to flow. Conductance given in units of W/m$^2$ K would be the inverse of the resistance, given in units of m$^2$ K/W. Conservation of heat is analogous to conservation of current. Heat flow into and out of any point sums to zero just as the sum of current into and out of any point in a circuit sums to zero. This analogy must be used with care in the case where we make use of heat flux (W/m$^2$). Heat flux accounts for the area through which the heat flows. The total heat flow is the product of the heat flux and the area through which it flows. Such distinction is necessary when considering the geometric effects of the device design. In FIG. 1, R1 represents the resistance of the body to heat flow. R2 is the resistance of heat flow through the device 120, and R3 represents the resistance of heat flow to move from the surface 125 of the device into the surrounding environment 151.

Using propagation of error for non-linear equations it is possible to create an approximate equation for error in $T_{core}$ as a function of error in the measurement of $T_{skin}$ and $T_{band}$. When the skin and insulator sensors are the same the errors for both can be assumed equal which leads to the following:

$$\sigma_{Tcore} = \sigma_{Tsensor}\sqrt{1 + 2\left(\frac{L_{band}}{L_{core}}\right) + 2\left(\frac{L_{band}}{L_{core}}\right)^2} \tag{2}$$

The ratio of $\sigma_{Tcore}$ to $\sigma_{Tsensor}$ is a signal to noise ratio. Temperature sensors with an accuracy of 0.1° C. are typical. Choosing a value of 1° C. for the device accuracy would result in a ratio of 10.

The thermal conductance of the body ($L_{core}$) is treated here as a fixed value. Thermal conductance is the ratio of the thermal conductivity to the material thickness so variations in either the thermal conductivity or the depth of the core temperature zone would correspond to changes in the thermal conductance of the body. Thermal conductivity of various components of the human body varies as shown in Table 1 (see Herman I. P. *Physics of the Human Body*. Springer, Berlin, 2007. p. 362.). The body conductance of interest refers to the volume-weighted average of all the components of the body between the skin sensor and the layer in the body at the core body temperature.

TABLE 1

| Tissue | Thermal Conductivity (W/m K) | Specific Heat (MJ/m K) |
| --- | --- | --- |
| Muscle-living | 0.642 | 3.94 |
| Skin - normal | 0.960 | 3.77 |
| Subcutaneous pure fat | 0.190 | 1.96 |
| Whole blood | 0.549 | 3.82 |

The depth ($D_{core}$) of the core body temperature depends on location on the body and differs subject to subject. It is possible to minimize the variation by choosing a location on the body where an artery is close to the surface of the body. The temporal artery is an ideal selection because variation in conductance is low. Experimental work was done to estimate a value for artery depth. A heat stress indicator device based on the design described in this patent was worn simultaneously with an ingestible core temperature sensor (Jonah capsule by Mini Mitter). It is possible to estimate the depth of the temporal artery using the core temperature measured by the capsule with the knowledge of the material properties of the device. A calculated value of 2.5 mm was determined for $D_{core}$.

As a person becomes more active and the core body temperature increases, vasodilatation occurs in the skin causing an increase in blood flow and an increase in thermal conductivity. The relationship between activity level, core body temperature, and thermal conductance is an important factor. Thermal conductivity of the skin for example changes from a value of 0.34 W/m K when cold to 0.96 W/m K when warm and even as high as 2.8 W/m K when very warm (see Robert A. Freitas Jr., Nanomedicine, Volume I: Basic Capabilities, Landes Bioscience, Georgetown, Tex., 1999, Table 8.12). Near the temporal artery, values of body conductance are expected to be between 20 and 200 W/m² K. In practice, the device would select a conductance value appropriate to the physiological state of the wearer.

The equation for estimating core temperature based on the one-dimensional model is given in equation (1). A generalized form of equation (1) may be shown as:

$$T_{core} = T_{skin} + A \cdot (T_{skin} - T_{band}) \quad (3)$$

The term 'A' being the ratio of the thermal conductance of the bandage to that of the core is therefore not strictly constant.

$$A = \frac{L_{band}}{L_{core}} \quad (4)$$

As the body heats up and vasodilatation occurs, the thermal conductance of the core increases and the value for 'A' is reduced. In practice values for 'A' would be chosen based on the physiological state of the subject. A look-up table can be produced by calculation based on blood perfusion as a function of core body temperature and the corresponding change in thermal conductivity of the core layer ($L_{core}$). Alternately such a table could be derived from experimental data covering the range of subjects so as to provide a table of 'A' values applicable to the population of expected wearers.

Figure 2:
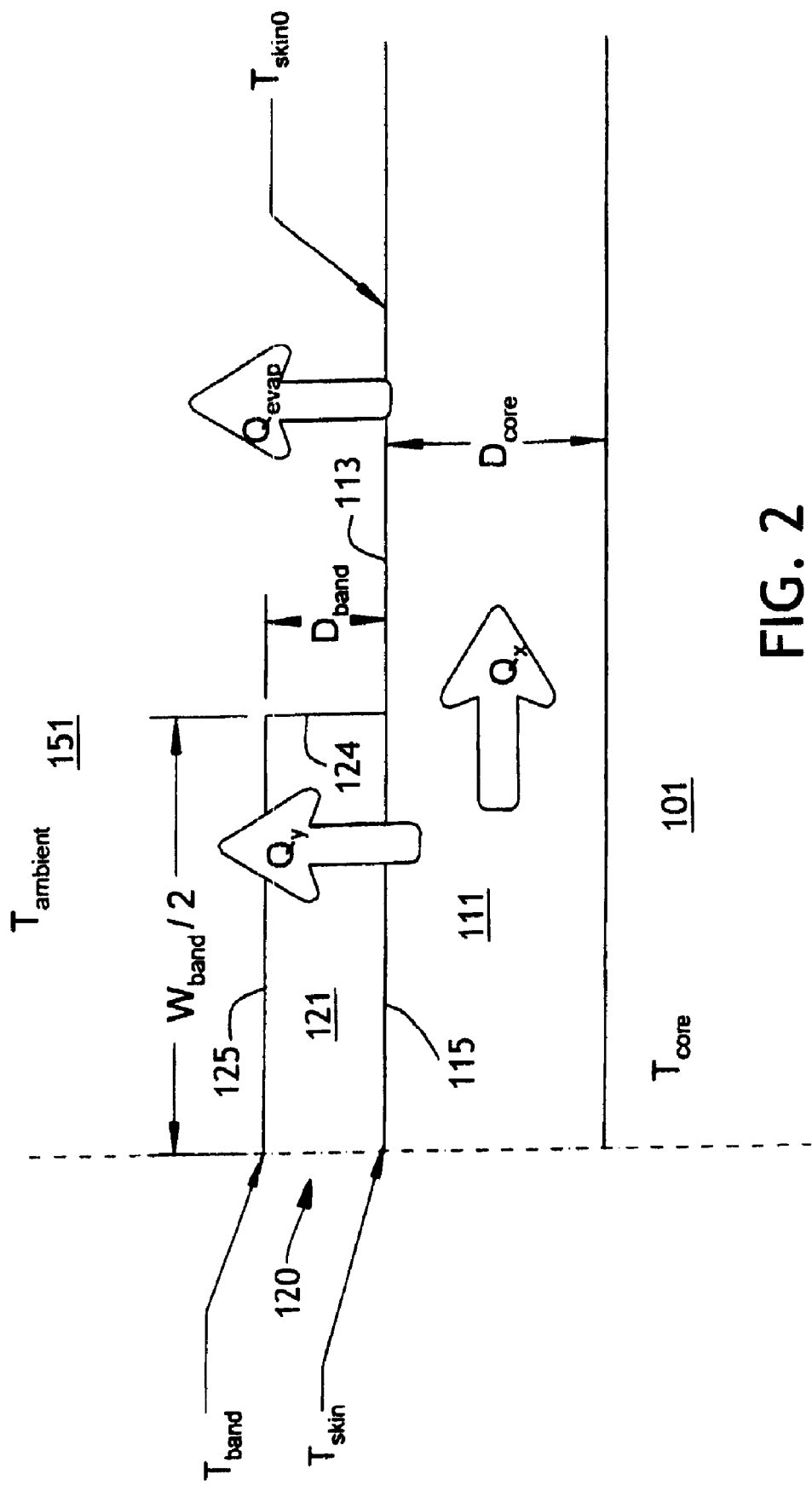
FIG. 2 illustrates a heat balance model used for determining parameters for thermal stress monitoring in accordance with the present disclosure.

Accounting for the heat loss around the heat stress indicator is an important factor when using the one-dimensional heat loss model. The accuracy of the one-dimensional model is dependent on an accurate estimate of heat flux from the body. One method for achieving this is to design the device with a thermal conductance that is large enough that the flux through the device is very close to the heat flux leaving the body. This necessarily requires a minimal heat flux around the device. In general terms, heat flux leaving the body can go through the device 120 or around the device 120. FIG. 2 shows a cross-section schematic model of the device 120 as applied to the body. The left side of FIG. 2 is an axis of symmetry. The bottom layer 101 represents the layer in the body that is at the core temperature. $Q_x$ is the heat moving around the device 120 in the body layer 111 between the skin surface 113 and the core temperature layer 101. $Q_y$ is the heat flow moving through the device 120. $Q_{evap}$ corresponds to any heat loss caused by evaporation of body moisture. $T_{ambient}$ represents the temperature of the surrounding environment 151. $T_{band}$ and $T_{skin}$ are the temperatures of the outer surface 125 and skin side surface 115 of the insulation layer 121 in the device 120, respectively. $T_{core}$ is the core body temperature and $T_{skin0}$ refers to the skin temperature at a point 113 on the skin just outside the perimeter of the device 120. It should be recognized that $T_{skin0}$ is lower than $T_{skin}$ because of the insulation layer in the device. Sweat produced by the body is prevented from evaporating under the device, but is unhindered outside the device causing a further reduction in skin temperature. The difference in skin temperature under the device from that just outside the device causes a heat flow in the direction indicated by $Q_x$. When the heat flux around the device ($Q_x$) is large with respect to the heat flux through the device ($Q_y$) the one-dimensional model fails to estimate core body temperature accurately.

Figure 3:
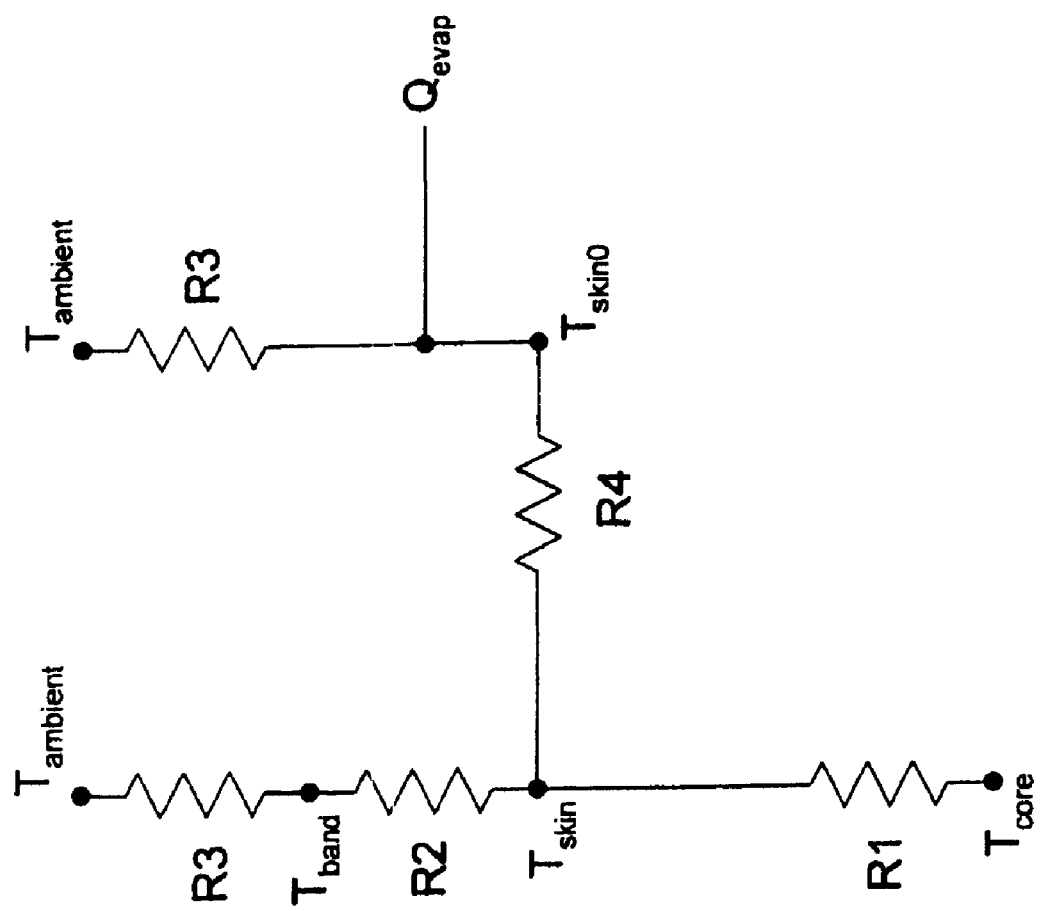
FIG. 3 illustrates a circuit diagram representative of the heat balance model of FIG. 2, in accordance with the present disclosure.

The drawing in FIG. 3 provides an analogous electrical circuit schematic for the geometry shown in FIG. 2. In the schematic of FIG. 3, R1 corresponds with the thermal resistance of the body, R2 corresponds with the thermal resistance of the device 120, and R3 corresponds with the resistance of heat leaving the surface 125 of the device into the surrounding environment 151. The resistor R4 represents the thermal resistance of the body around the device. The term $Q_{evap}$ corresponds to evaporative heat loss and is analogous to a specified current drain in the circuit. In this system the heat flow leaving the core may be written as:

$$Q_y = k_{core} \cdot \frac{W_{band}}{2} \frac{(T_{core} - T_{skin})}{D_{core}} \quad (5)$$

Where $k_{core}$ is the thermal conductivity of the body layer 101, $T_{core}$ and $T_{skin}$ are the core and skin temperatures respectively, and where $D_{core}$ is the depth to the core body temperature layer 101. The heat flow $Q_y$ is in J/sec or watts. Referring again to FIG. 2, the term $W_{band}/2$ is the distance between the sensor measurement of $T_{skin}$ and/or $T_{band}$ and the outer or peripheral edge 124 of the insulation layer 121. In the case that the measuring sensors are directly in the middle of the insulation layer 121 then $W_{band}$ would correspond to the minimum device width. For the sake of simplifying the discussion, $W_{band}$ is often referred to as the "width" of the device. However, for devices in which the measuring sensor(s) are not in the geometric center of the insulating layer, $W_{band}/2$ is the distance the sensors are from the peripheral edge 124 of the insulating layer 121.

The heat flow moving around the device ($Q_x$) is approximately:

$$Q_x = k_{core} \cdot D_{core} \frac{2 \cdot (T_{skin} - T_{skin0})}{W_{band}} \quad (6)$$

Where $T_{skin0}$ is the temperature of the skin at the outside edge of the device 120. The heat flow $Q_x$ is in J/sec or watts.

Approximate values for $T_{skin}$ and $T_{skin0}$ can be calculated by considering the steady state condition at two different locations. We will consider the case where the heat flux through the body layer is the same as the flux through the device, which is in turn equal to the heat lost into the environment 151.

$$\frac{k_{core}}{D_{core}}(T_{core} - T_{skin}) = \frac{k_{band}}{D_{band}}(T_{skin} - T_{band}) \quad (7)$$
$$= h(T_{band} - T_{ambient})$$

Thermal conductance of the core ($L_{core}$) is the ratio of the bodies thermal conductivity ($k_{core}$) to the depth ($D_{core}$) of the core temperature zone 101. Similarly the conductance of the insulation ($L_{band}$) is the ratio of the thermal conductivity ($k_{band}$) of the insulation layer 121 to its thickness ($D_{band}$). The heat lost into the environment 151 from the outer surface 125 of the device 120 is proportional to the difference in the outer surface 125 temperature ($T_{band}$) and the outside temperature ($T_{ambient}$). The proportionality constant (h) is a transfer coefficient and has a value of approximately 9 W/m K, for people in nominal inside work conditions. Solving these equations provides a direct expression for $T_{skin}$ and for $T_{band}$.

$$T_{skin} = \frac{\begin{array}{c}D_{core} \cdot h \cdot k_{band} \cdot T_{ambient} + \\ k_{core} \cdot T_{core}(D_{band} \cdot h + k_{band})\end{array}}{D_{core} \cdot h \cdot k_{band} + k_{core} \cdot (D_{band} \cdot h + k_{band})} \quad (8)$$

$$T_{band} = \frac{\begin{array}{c}D_{core} \cdot h \cdot k_{band} \cdot T_{ambient} + \\ D_{band} \cdot h \cdot k_{core} \cdot T_{ambient} + k_{band} \cdot k_{core} \cdot T_{core}\end{array}}{D_{core} \cdot h \cdot k_{band} + D_{band} \cdot h \cdot k_{core} + k_{band} \cdot k_{core}} \quad (9)$$

At steady state and at a distance away from the device the heat flux leaving the skin 113 is equivalent to the heat entering the surrounding environment plus the heat lost from evaporation.

$$\frac{k_{core}}{D_{core}}(T_{core} - T_{skin0}) = h(T_{skin0} - T_{ambient}) + Q_{evap} \quad (10)$$

Rearranging this equation produces an expression for $T_{skin0}$.

$$T_{skin0} = \frac{k_{core} \cdot T_{core} + D_{core} \cdot h \cdot T_{ambient} - D_{core} \cdot Q_{evap}}{D_{core} \cdot h + k_{core}} \quad (11)$$

Substituting the expressions for $T_{skin}$, $T_{band}$, and $T_{skin0}$ (equations 8, 9, and 11) into equations (5) and (6) and simplifying produce the following:

$$Q_x = \frac{2 \cdot D_{core}^2 \cdot k_{core}(D_{core} \cdot h \cdot k_{band} \cdot Q_{evap} + k_{core}(k_{band} \cdot Q_{evap} + D_{band} \cdot h \cdot (Q_{evap} + h(T_{core} - T_{ambient}))))}{(D_{core} \cdot h + k_{core})(D_{core} \cdot h \cdot k_{band} + k_{core}(D_{band} \cdot h + k_{band})) \cdot W_{band}} \quad (12)$$

And $$Q_y = \frac{h \cdot k_{band} \cdot k_{core} \cdot W_{band}(T_{core} - T_{ambient})}{2(D_{core} \cdot h \cdot k_{band} + k_{core}(D_{band} \cdot h + k_{band}))} \quad (13)$$

The ratio of the heat flows $Q_x/Q_y$ can be simplified to the following expression:

$$\frac{Q_x}{Q_y} = \quad (14)$$

$$4 \cdot \frac{\begin{array}{c}D_{core} \cdot h \cdot k_{band} \cdot Q_{evap} + k_{core} \cdot \\ (k_{band} \cdot Q_{evap} + D_{band} \cdot h \cdot (Q_{evap} + h \cdot (T_{core} - T_{ambient})))\end{array}}{h \cdot k_{band} \cdot (D_{core} \cdot h + k_{core})(T_{core} - T_{ambient})} \cdot \left(\frac{D_{core}}{W_{band}}\right)^2$$

This expression can be further simplified by considering the case where the core body temperature ($T_{core}$) is at 36.8° C., the ambient environment temperature ($T_{ambient}$) is at 27° C., the transfer coefficient (h) is 9 W/m K, the core body depth ($D_{core}$) is 0.0025 m, and the thermal conductivity of the body ($k_{core}$) is at 0.43 W/m K. The resulting simplified equation (14) for the ratios of heat flows is:

$$\frac{Q_x}{Q_y} = 4\left(\frac{7.209}{L_b} + \left(0.0118 + \frac{0.1101}{L_b}\right) \cdot Q_{evap}\right)\left(\frac{D_{core}}{W_{band}}\right)^2 \quad (15)$$

Equation (15) can be inverted to provide an estimated $W_{band}$ distance required to achieve a particular Q-ratio ($Q_x/Q_y$) or less.

$$Q_{ratio} = \frac{Q_x}{Q_y} \quad (16)$$

$$W_{band} > \frac{0.02 \cdot D_{core}\sqrt{72090 + 1101 \cdot Q_{evap} + 118 \cdot L_b \cdot Q_{evap}}}{\sqrt{L_b \cdot Q_{ratio}}} \quad (17)$$

The amount of error caused by heat flow around the device can be estimated by considering how the device would calculate core temperature. A device that uses the simple one-dimensional model uses the temperature drop across the insulation layer to estimate body heat flux. The general formula is equation (1). Excessive heat loss around the product causes the actual temperature drop across the insulation value to be reduced and the corresponding estimate of core body temperature to be low. The heat drop across an insulator is:

$$\Delta T = \frac{Q \cdot D}{k} = \frac{Q}{L} \quad (18)$$

Where 'k' is the thermal conductivity, 'D' is the thickness of the layer, and 'Q' is the heat flux. Consider the case where there is no added heat loss around the device.

$$\Delta T_{noloss} = \frac{Q_{band}}{L_{band}} \quad (19)$$

In the case where some of the heat flux is diverted around the device. The resulting flux through the device is reduced and the corresponding impact on the measured temperature drop would be:

$$\Delta T_{loss} = \frac{Q_{band} - Q_x}{L_{band}} \quad (20)$$

The error in core temperature estimation due to this diverted heat would be the difference between the temperature estimate with and without the diverted heat.

$$TcoreError = \quad (21)$$
$$\left(T_{skin} + \frac{L_{band}}{L_{core}} \frac{Q_{band}}{L_{band}}\right) - \left(T_{skin} + \frac{L_{band}}{L_{core}} \frac{(Q_{band} - Q_x)}{L_{band}}\right) = \frac{Q_x}{L_{core}}$$

The combined constraints described in equations (3), (15) and (21) provide guidance for developing a heat stress indicator that accommodates some level of sweat loss from the skin around the device while remaining within given device accuracy targets.

Figure 4:
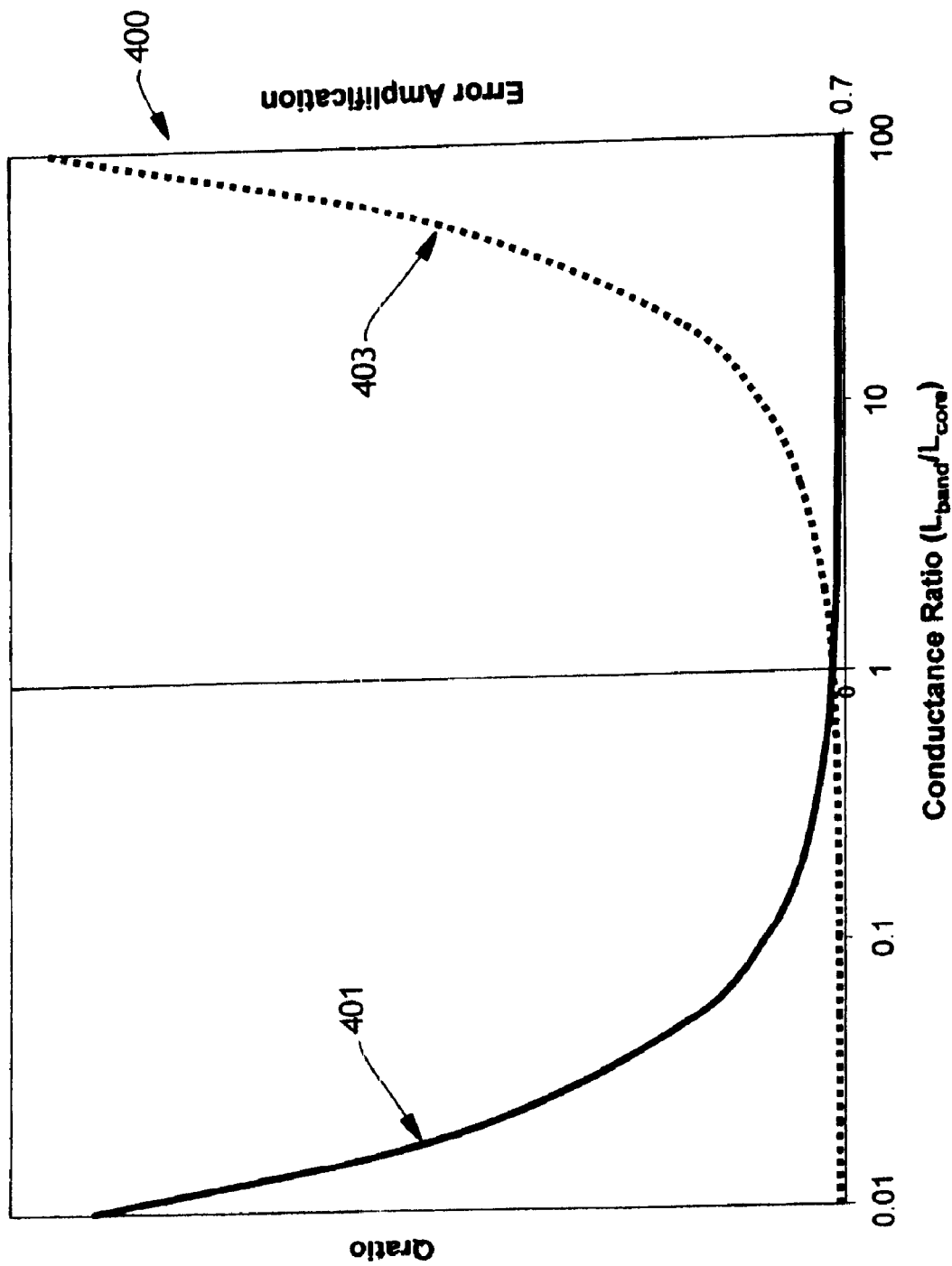
FIG. 4 is a plot that illustrates the optimization of the conductance ratio for the materials of the thermal stress monitoring device as a balance between device error and the heat transfer ratio as is in accordance with the present disclosure.

The design constraints are based on two design choices; the desire to use the one-dimensional model of heat flow and an overall accuracy target for the product. These constraints are characterized in FIG. 4 as two competing functions of the ratio of the thermal conductance of the device to the conductance of the body. This ratio 'A' as described in equation (3), has implications on error caused by the sensitivity limitations of the temperature sensing devices as described in equation (2). A reduction in the device thermal conductivity has a corresponding reduction in 'A'. At low thermal conductance, the temperature drop across the insulator 121 is maximized. The ratio of noise (i.e., the error from the temperature sensors) to the signal (i.e., the temperature drop across the insulator layer 121) is maximized and the error is minimized. This is shown as the "Error Amplification" curve 403 in FIG. 4. However, as 'A' is reduced corresponding to lower thermal conductivity of the device 120 less of the heat from the body is moving through the device 120 and more heat moves around it. This corresponds to an increase in $Q_{ratio}$ ($Q_x/Q_y$) as shown as the "Qratio curve" 401 in FIG. 4. The implication of FIG. 4 is that there is an optimum conductance ratio (A) for minimizing the two types of device error.

Figure 5:
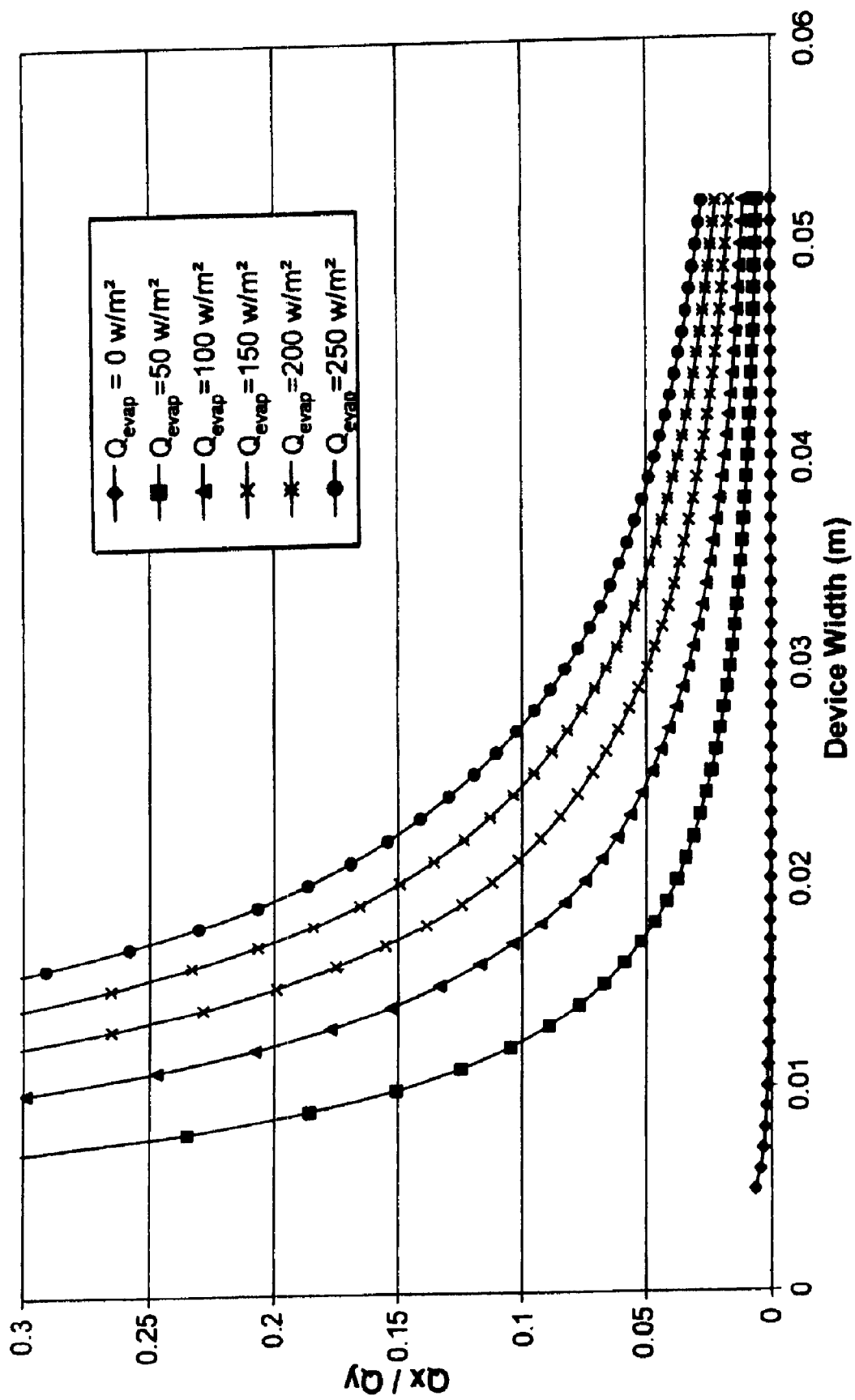
FIG. 5 is a plot that illustrates the selection of the device width in accordance with the present disclosure.

As described in equation (15), the ratio of heat flow around ($Q_x$) and through ($Q_y$) the device is a function of both the product width and the amount of evaporative heat loss on the skin. This relationship is shown graphically in FIG. 5 where the impact of evaporative heat loss is described for a device with a specified thermal conductance (where $L_{band}$=1127 W/m² K). This relationship demonstrates the ability to accommodate a given amount of evaporative heat loss by changing the size of the device. The appropriate choice of $Q_x/Q_y$ to minimize error requires some additional estimation as shown below.

The following provides an example of the combined use of these derived equations to develop size and material properties for a heat stress indicator. An estimate of body conductance is given by:

$$L_{core} = \frac{k_{core}}{D_{core}} = \frac{0.43}{0.0025} = 172 \frac{W}{m^2 \cdot K} \quad (22)$$

Here a volume weighted average for core thermal conductivity ($k_{core}$) is 0.43 W/m K and the depth of the temporal artery ($D_{core}$) is taken to be 2.5 mm. This value of $L_{core}$ can be substituted into equation (21). The value $T_{coreError}$ will be set to be about ⅓ of the tolerable error of 1° C.

$$TcoreError = \frac{Q_x}{172} \quad (23)$$

$$\frac{Q_x}{172} \le 0.3 \quad (24)$$

$$Q_x \le 52 \quad (25)$$

A reasonable upper end range for $Q_y$ is 250 W/m². This provides a rough estimate for an acceptable ratio of $Q_x$ to $Q_y$ at 0.21 or less. Non-acclimatized subjects working at a rate >65 W/m² are at the upper range of their thermal strain when sweating at 650 g/hr which corresponds to 250 W/m² of evaporative loss (see Doherty, T. J., and E. A. Arens. 1988. "Evaluation of the Physiological Bases of Thermal Comfort Models." ASHRAE Transactions, Vol. 94, Part 1, 15 pp).

Further, consider the case where the desired goal is for the error in core temperature estimates to remain at or below 1° C., and where the selected temperature sensors have an error of 0.1° C. Substituting these values into equation (2) generates the following:

$$10 \ge \sqrt{1 + 2\left(\frac{L_{band}}{172}\right) + 2\left(\frac{L_{band}}{172}\right)^2} \quad (26)$$

This equation is true when $L_{band}$>1127 W/m² K. Neoprene has a nominal thermal conductivity of 0.2 W/m*K. A layer of neoprene 0.2 mm thick would provide such a thermal conductance.

Substituting these values into equation (14) generates the following relationship.

$$0.21 = 4\left(\frac{7.209}{1127} + \left(0.0118 + \frac{0.1101}{1127}\right) \cdot Q_{evap}\right)\left(\frac{0.0025}{W_{band}}\right)^2 \quad (27)$$

As discussed earlier a value of 250 W/m² is a reasonable upper end value for $Q_{evap}$. Using this value of $Q_{evap}$ it is possible to solve for $W_{band}$. In this case the value is 0.019 meters, or just under 2 cm.

Thus, a thermal stress monitoring device containing sensors with a nominal accuracy of 0.1° C. sandwiched between a 0.2 mm layer of neoprene having a thermal conductivity of 0.2 W/m*K with no sensor nearer than 2 cm from any edge of the neoprene would maintain a core temperature error of less than 1° C. on a subject that is sweating at a rate such that 250 W/m² or less of evaporation was taking place around the device.

An alternate example could be a thermal stress indicator designed to less stringent evaporative heat loss values of 150 W/m². In this example, soft vulcanized rubber may be used and it has a nominal thermal conductivity ($k_{band}$) of 0.138 W/m K. Sensor accuracy of 0.1° C., and overall device accuracy target of 1° C. remain the same. The constraint from equation (2) provides a target insulator layer conductance at the same value of 1127 W/m² K. In the case of the rubber material this corresponds to a layer thickness of 0.005 inches. Making use of equation (15) this time with the reduced $Q_{evap}$ value of 150 W/m² generates a $W_{band}$ value of 1.46 cm. This example design maintains $T_{core}$ error at or below 1° C. for a subject sweating at or below 150 W/m² which corresponds to a moderate sweat level.

Figure 6:
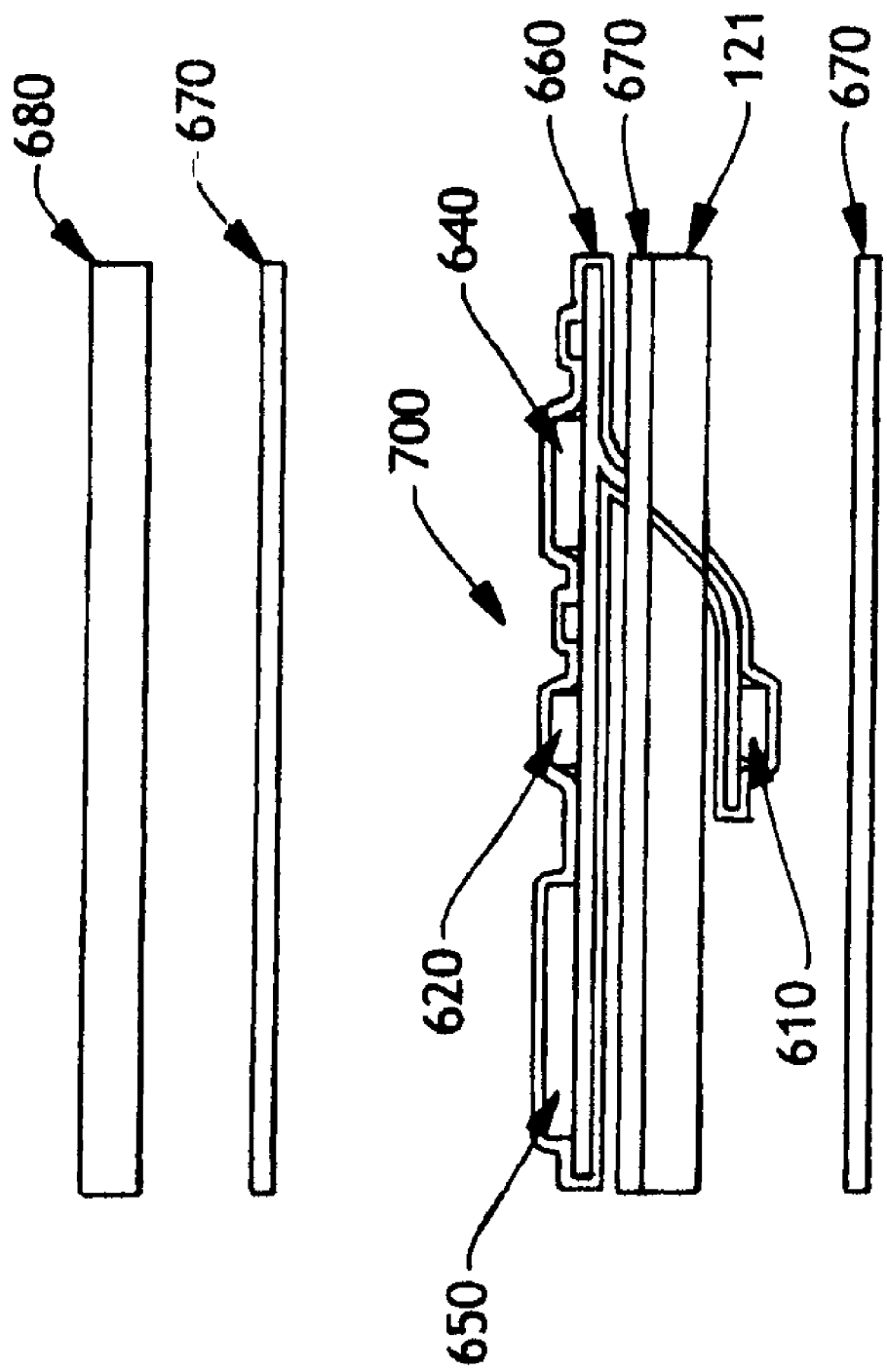
FIG. 6 is an exploded cross-sectional schematic view of a thermal stress monitoring device in accordance with the present disclosure.

As shown above, the design of the insulating layer 121 is important to the success of the device of the present disclosure. Other components are also present in the thermal stress monitoring device of the present disclosure. As illustrated in FIG. 6, the thermal stress monitoring device 600 includes several components such as multiple temperature sensors 610, 620, an onboard microprocessor 640, and an onboard power supply 650, in addition to the insulating layer 121.

To effectively estimate core body temperature, two temperature measurements are necessary. These measurements include the skin surface temperature and the temperature at a fixed distance through an insulating material layer of known thermal properties, for an estimation of heat flux across the device. It may also be desirable to include more than one skin surface sensor to minimize the affects of device placement in relation to the temporal artery where it is expected that the sensor nearest the temporal artery will indicate the highest temperature. The sensors used for measurements could include, but are not limited to, a thermistor in either a Wheatstone Bridge configuration or a simple voltage divider configuration, the p-n junction of a very inexpensive rectifier diode, or a solid state temperature sensing integrated circuit such as the ADT75 or ADT7302 both produced by Analog Devices Corporation.

Figure 7:
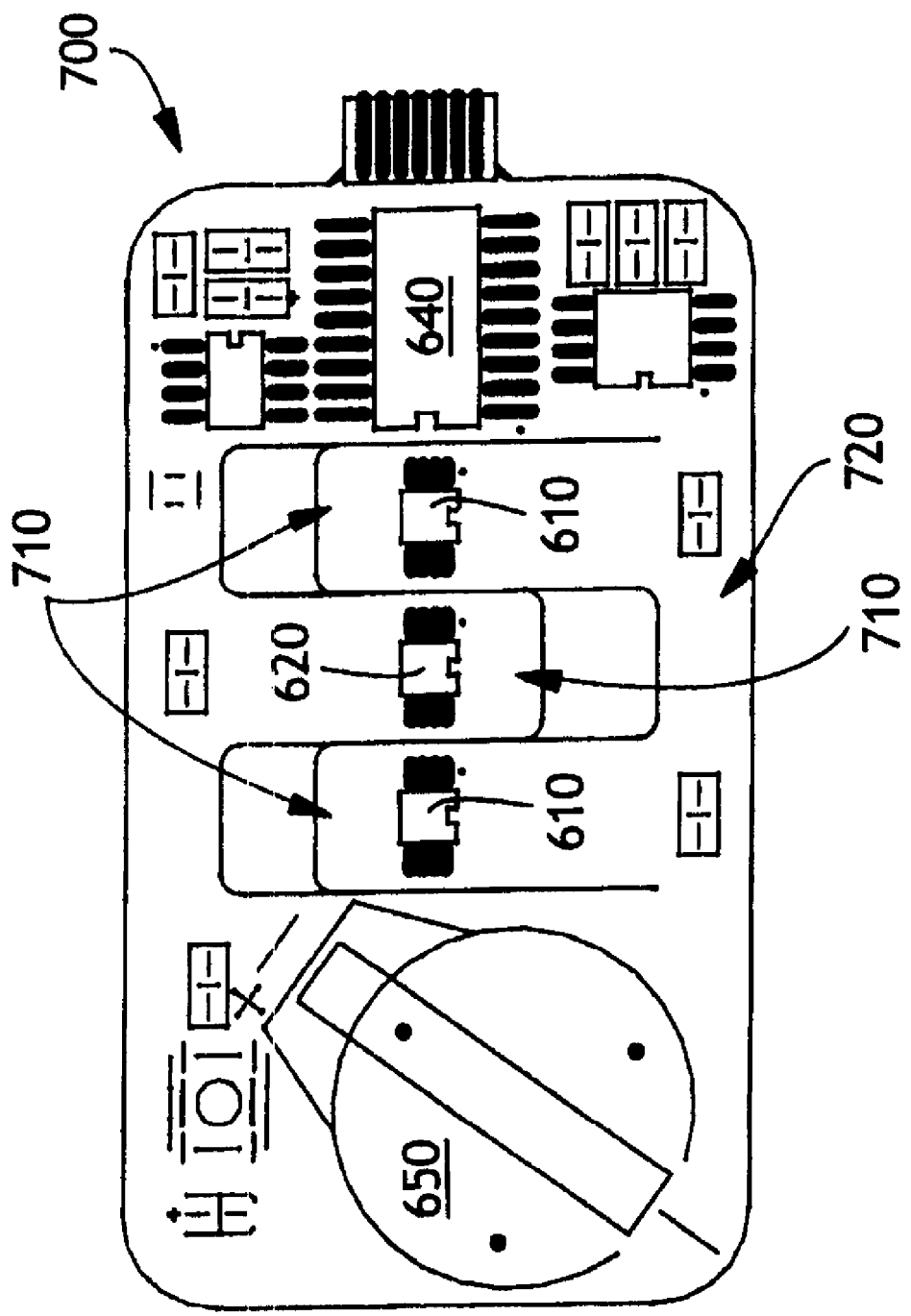
FIG. 7 is a planar top view of a circuit board for a thermal stress monitoring device in accordance with the present disclosure.

In one embodiment two temperature sensors are used; a first temperature sensor 610 in contact with the skin surface and a second temperature sensor 620 on the opposite side of an insulating layer 121 of known thickness and known thermal properties. The device 600 is configured such that the insulating layer 121 is positioned between the sensors 610, 620 and separates the first temperature sensor 610 from the second temperature sensor 620. The first and second temperature sensors 610, 620 and insulating layer 121 are configured to be in thermal communication with one another. As used here, the term "thermal communication" refers to the condition where the temperatures of the sensor side of the sensor/insulating layer boundary is substantially equal to the temperature of the insulating layer side, or in other words there is approximately no temperature difference between the two materials at the boundary in which they are in thermal communication. The first and second temperature sensors 610, 620 may be aligned in the general direction of heat flux or they may be proximate to each other and offset. For example, in another embodiment, the first temperature sensors 610 may be in an interlocked positioning scheme where a pair of first temperature sensors 610 is offset from one another with the second temperature sensor 620 placed half way between the pair of first temperature sensors. The insulating layer (not shown in FIG. 7) would then be positioned, relative to the user's skin, above (or over) one of the first temperature sensors 610, below (or under) the second temperature sensor 620, and then above (or over) the other first temperature sensor. The temperature sensors 610, 620 may be placed centrally amongst the circuit board 700 on fingerlike protrusions 710 from the edge 720 of the circuit board substrate. These fingerlike protrusions allow for multiple first temperature sensors 610 to penetrate the thermal insulating layer and allow for skin surface temperature measurements while the remaining second temperature sensor(s) remain on the circuit side of the thermal insulating layer to supply the appropriate $T_{band}$ measurement with minimal affects on the flexibility of the overall device.

The insulating material 121 may be any flexible material having the specific thermal characteristics and designed dimensions as is desired for the particular device desired, as discussed above. For example, neoprene and vulcanized rubber are examples of insulating materials that may be used for the thermal stress monitoring device 600.

The onboard processor 640 is configured to perform the tasks of collecting temperature data from the multiple temperature sensors via either analog to digital converter input channels or serial communication busses providing RS-232, SPI, or I²C communication capabilities, processing the data, determining whether an thermal stress alarm is warranted, and outputting an alarm signal, if necessary. A low-power processor can be utilized since processing power requirements are relatively low. The processor collects data from the multiple temperature sensors on a fixed time interval and implements an algorithm to predict the core body temperature. Several core temperature values are maintained in a first-in-first-out (FIFO) data buffer to facilitate calculations in estimating a temperature change over time. Examples of possible processors include the MSP430 Ultra-low Power Microcontroller available from Texas Instruments (Dallas, Tex.) or the PIC16F689 8-bit PIC® Microcontroller available from Microchip Technology, Inc. (Chandler, Ariz.).

Figure 8:
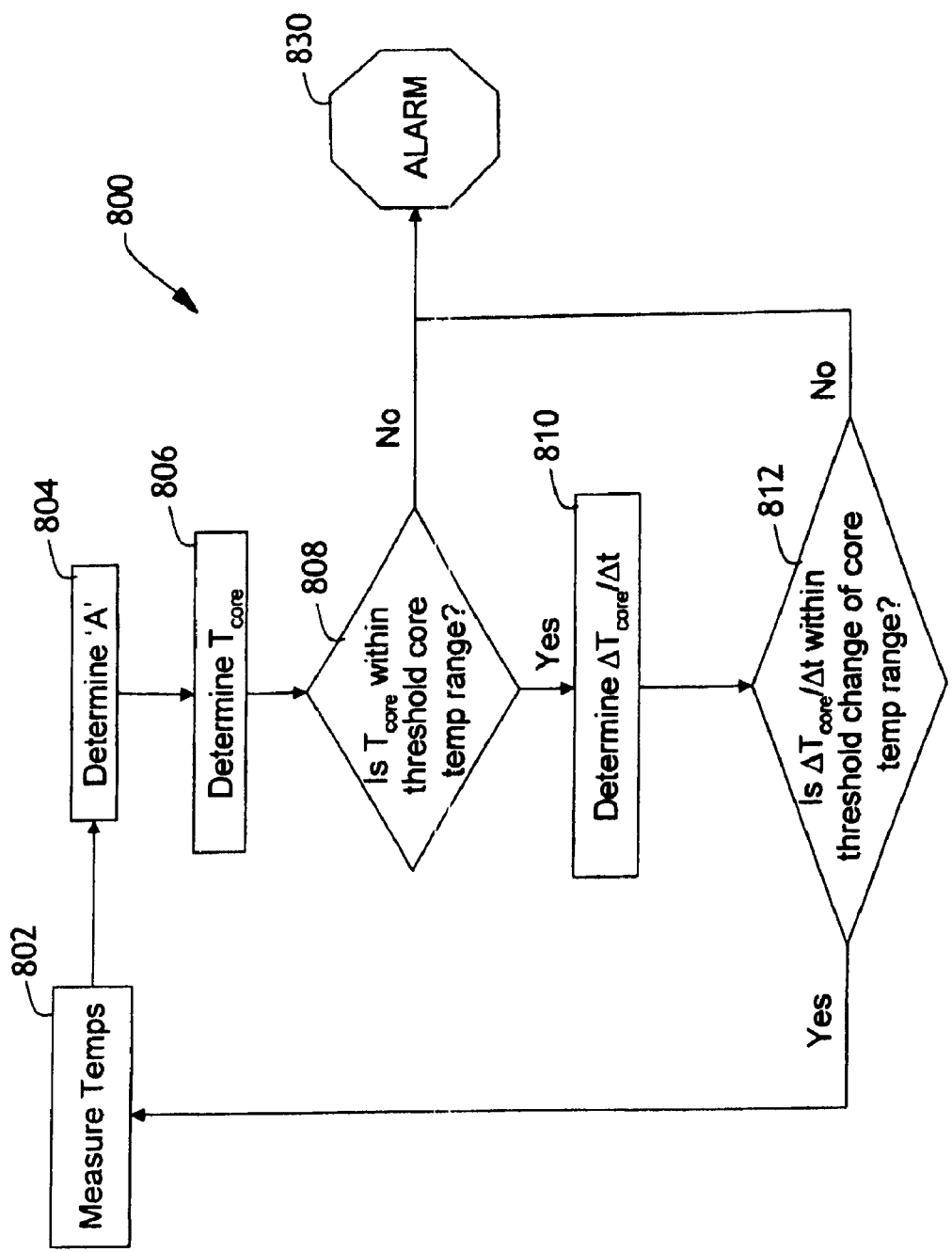
FIG. 8 illustrates a method for monitoring thermal stress in accordance with present disclosure.

In practice the thermal stress device 600 would execute a decision algorithm 800, such as illustrated in FIG. 8. As a first step 802, the first and second temperature sensors 610, 620 measure their respective temperatures. At step 804 the value of 'A', the ratio of insulating layer conductance to core conductance is determined, as discussed above. Next, in step 806 the core temperature is determined using equation (1). Then, in step 808 the determined core temperature is compared with a stored threshold temperature range. If the determined core temperature is outside of the threshold temperature range, an alert signal 830 is generated.

The stored threshold temperature range is the body core temperature range in which it is desired that the body core temperature is maintained. Such a threshold temperature range may include the limiters of standard temperatures given for heat stress and hypothermia. For example, the threshold temperature range may be 38° C. to 35° C. Such a threshold temperature range may be designed to be narrower or wider depending on when various thermal stress alerts may be desired.

Similarly, in step 810 the change in core temperature over a known period of time is determined. The determined change in core temperature from step 810 is then compared with a stored threshold change in core temperature range, in step 812. If the determined change in core temperature is outside of the threshold change in temperature range, an alert signal 830 is generated.

The stored threshold change in core temperature range is the rate of change in the body core temperature in which it is desired to be maintained. Generally, the range will extend from zero to some maximum rate of change considered to indicate a thermal stress condition. For example, the threshold change in body temperature range may be 0 to 1.5° C./hr.

The decision algorithm 800 would then return to step 802 and another set of temperature measurements would be collected, and the algorithm 800 would continue.

Figure 9:
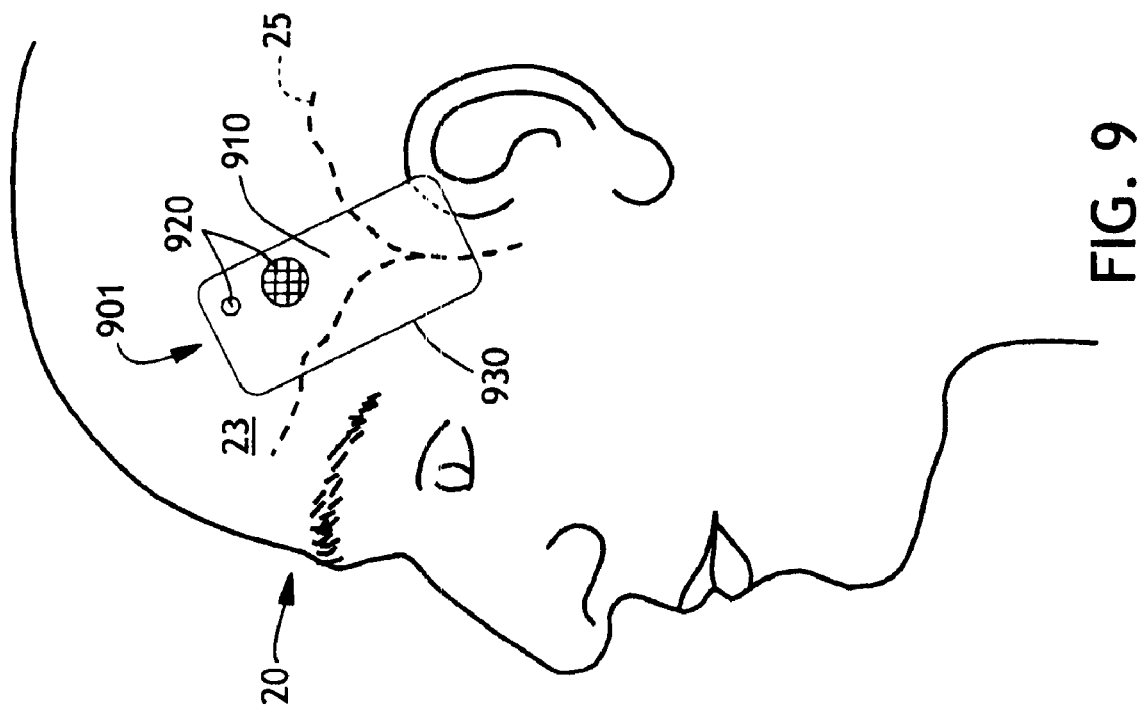
FIG. 9 is a perspective view of a thermal stress monitoring device in accordance with the present disclosure placed proximate the temporal artery of a user.
Figure 11:
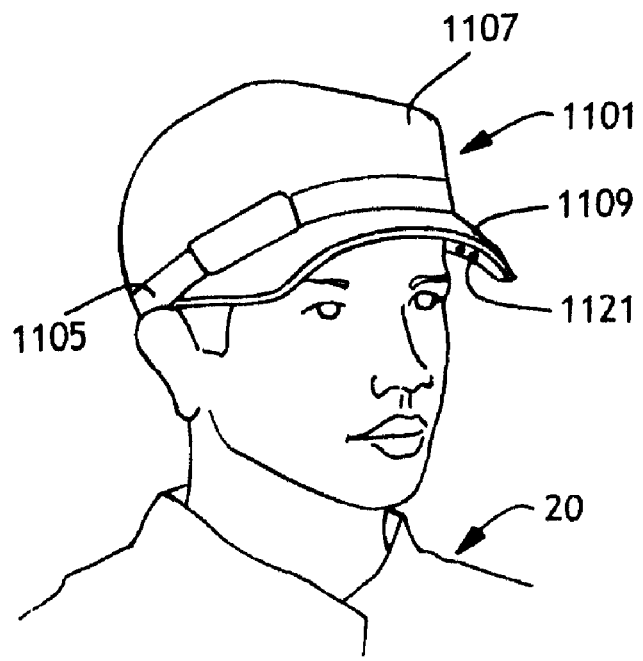
FIG. 11 is a perspective view of a thermal stress monitoring device, in accordance with the present disclosure, incorporated in the hatband of a cap.

If either the determined core body temperature or the determined change of core body temperature over a fixed period of time falls outside the threshold ranges which indicate the onset of thermal stress, the microprocessor generates an alarm output 830. The thermal stress monitoring device may also include an alarm device. As shown in FIG. 9, such an alarm device 920 may be present on the thermal stress monitoring device 910 itself. Alternatively, in some embodiments, the device may be configured to provide the alarm signal to an alarm device that is separated from the device. For example, for a thermal monitoring device placed on a user's forehead/temple, the alarm device may be an LED separated from the device by a short distance such that the alert device may be in the user's field of vision. The monitoring system 1101 illustrated in FIG. 11 shows such a separated alarm device 1121 on the brim 1109 of a cap 1107 while the monitoring device 1110 is positioned on the hatband 1105 of the cap 1107. In another example, for the same monitoring device on a user's forehead, the alarm device may be included in a wristband worn by the user.

The monitoring device may also include a transmitter that transmits such an alarm signal to a remote alarm device. For example, such a remote alarm device may be an alarm device worn by another user in the same location or in a different location. In another example, the remote alarm device may be a centralized monitoring station. Such remote monitoring may preferably be used in conjunction with an alert provided to the user or may be used as a replacement to alerting the user.

The alarm may include any means that stimulates one of the human senses to gain the attention of the user. For example, the alarm may include an audible alarm such as a tone generator, playback of a stored spoken message, a piezoelectric buzzer, or the like. The alarm may be a tactile alarm such as a vibration, or a visual alarm such as a blinking light, colored LEDs, a alpha-numeric display, or the like. The alarm may include a combination of any, or all, such alarms. For example, the alarm may include a blinking colored LED along with a vibrating piezoelectric buzzer. Alternatively, the alarm may include a tone generator along with an LED display that displays the determined body core temperature. The alarm should be capable of notifying the wearer of the alarm condition, but must also consume minimal amounts of power.

In one optional embodiment, the thermal stress monitoring device may provide a different alerts based upon specific thresholds. In addition to the threshold core temperature range and threshold change in core temperature range, the device may include stored warning ranges. Such warning ranges may be core temperatures or changes in core temperature within the threshold ranges, but may be included to warn the user of situations where the user's core temperature and/or change in core temperature is approaching the limits of threshold ranges. When the limits of such warning ranges were crossed, the device would then create a warning signal. The warning signal would then trigger a warning alarm. Such a warning alarm may utilize the same alarm utilized for the previously discussed threshold range alarm, it may use such a threshold alarm in a different way, it may utilize a warning alarm device separate from an alarm device for the threshold range alarms, or may use some combination thereof. For example, the thermal stress monitoring device may include a series of differently colored LEDs such that a warning alarm may be signaled by a yellow LED and a threshold range alarm may then be signaled by a red LED. In an alternate example, the warning alarm may include a blinking light and an audible beep every 30 seconds and if the threshold range is exceeded the light may switch to a more rapid blinking, the beep may become a sustained tone, and an additional alert signal may be sent to a remote alarm device. One skilled in the art would understand that various types and executions of warning alarms and threshold range alarms may be utilized to meet the particular needs of various users and environments of use.

In addition to the various types of alarms that may be utilized, in some optional embodiments, the alarm device may be continue to produce its alarm until the monitoring device determines that the core temperature, or change in core temperature, returns to within the appropriate threshold range. Alternatively, the alarm device may continue until the alarm device is reset. Such a reset may be included in the alarm device and may be reset by the user or may be configured such that the alarm may only be reset by another person (e.g., by a supervisor, safety officer, or a trainer). In another optional embodiment, the alarm may be reset only by relocating the user (and device) to a different location. Such alarm resets may be any combination of such options as desired by the particular user needs and/or particular safety accountability desired.

In another optional embodiment, the thermal stress monitoring device may include a thermal proximity alert to provide an alert signal when it is determined that the thermal stress monitoring device is not in thermal contact with the user. Such an alert may be given to the user to inform them of the need to reattach or reposition the device. Similarly, or alternatively, an alert signal may be sent to remote alert device to advice another person to check the status of the user.

Since the entire circuit is designed to minimize power, the power supply 650 can take on many forms. Additional criteria for the selection of the power supply device allow for the device to be disposable without contaminating the environment and provide sufficient power to supply the device for the entire useful life of the product. Examples of such power sources include, a lithium-ion coin cell battery, flexible thin film batteries, super capacitors, or one of several available energy harvesting devices coupled with a storage capacitor.

All components of the circuit 700 are to be constructed on a flexible substrate to allow for maximum flexibility of the circuit 700. Such a flexible circuit allows the device to conform to the wearer's body so that the first temperature sensor 610 may be held in thermal contact with the user's skin. In some embodiments the flexible substrate may be a flexible polyimide substrate. The thermal stress monitoring device 600 may also include a coating 660 that covers the elements of the circuit 700 from moisture or other damage. Additionally, the layers of the device may be joined by any method as known in the art for the construction of such devices. For example, appropriate adhesives 670 may be used to join the various layers of the device. Finally, an outer spacer layer may be included to protect the internal components of the device 600. Such an outer layer 680 may be an additional layer of insulating material provided to both protect the components and provide the device with insulation from the exterior environment. The circuit 700 described above along with the insulating layer 121 and an additional covering 680 of the insulating layer to minimize the affects of ambient conditions can be implemented in multiple forms.

The overall size and shape of the thermal stress monitoring device may be any size or shape that is desired for the particular user, user environment, and the needs of any particular monitoring system such a device is desired to be used. Such monitoring systems may include a garment that is worn by the user and that is configured to place the monitoring device in thermal contact with the skin of the user. In the embodiment shown in FIG. 9, the thermal stress monitoring device 910 may be incorporated into bandage 901 that may be affixed directly to the forehead 23 of a user 20, proximate the temporal artery 25. In such an embodiment, the device 910 may include a flexible backing substrate 930 and adhesive layer that holds the device 910 affixed to the skin of the user 20. The adhesive used may be any adhesive, as are well-known, that is strong enough to hold the device on the skin while the user perspires, but allows the device to be removed from the user. In other embodiments, the device may be integrated into other garments. For example, the device may be integrated into personal protective garments, which a worker may normally wear, such a safety eyewear, a hardhat, a welding helmet, or a cap. Similarly, the device may be incorporated into a sweatband or into the hood for protective coveralls.

Figure 10:
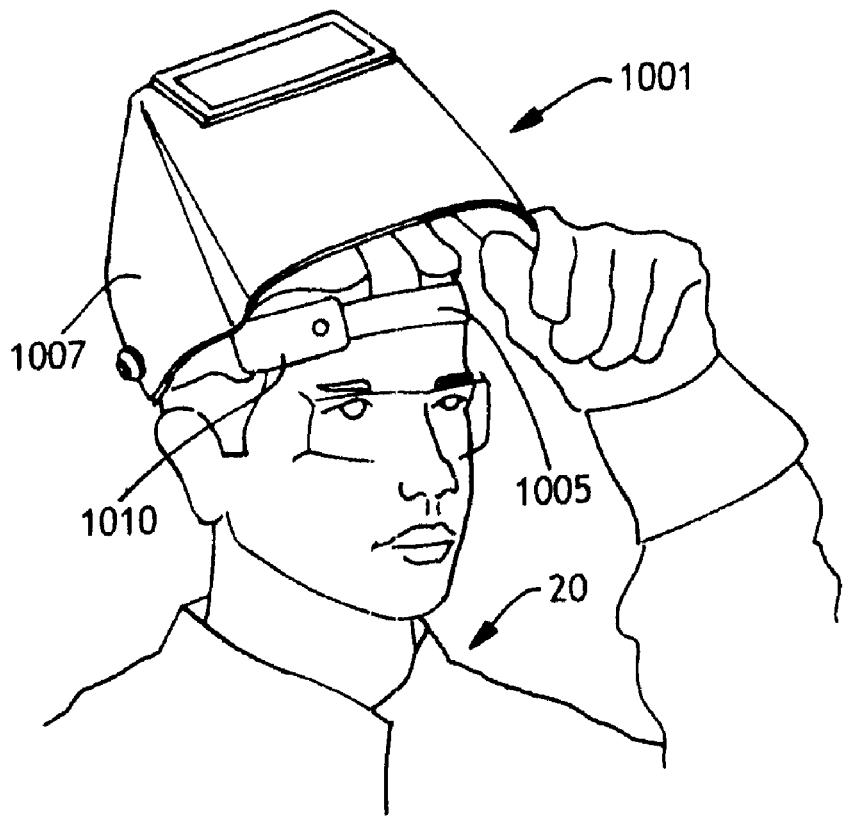
FIG. 10 is a perspective view of a thermal stress monitoring device, in accordance with the present disclosure, incorporated into the headband of a welding helmet.
Figure 12:
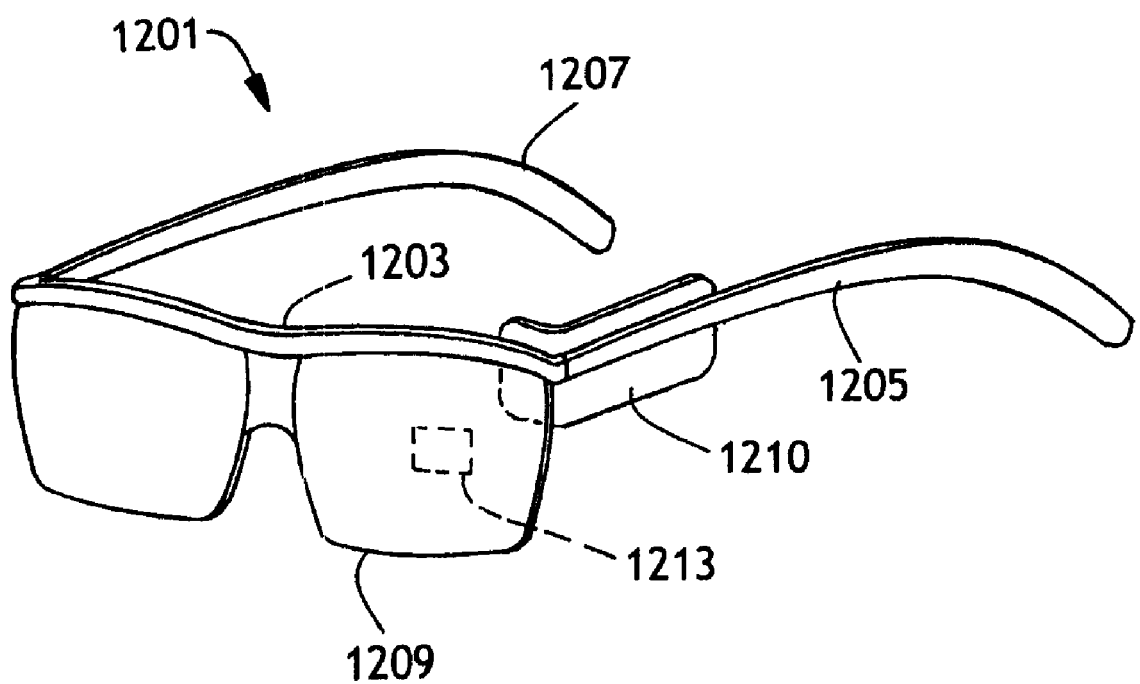
FIG. 12 is a perspective view of a thermal stress monitoring device, in accordance with the present disclosure, incorporated into eyewear.

Other optional embodiments of thermal stress monitoring systems are illustrated in FIGS. 10-12. FIG. 10 illustrates a welding helmet monitoring system 1001 where a thermal stress monitoring device 1010 is build into the headband 1005 of the welding helmet 1007. The device 1010 is positioned within the headband 1005 such that the device 1010 is proximate the temporal artery when the helmet 1007 is on the head of the user 20. A cap monitoring system 1101 is illustrated in FIG. 11, and includes a thermal stress monitoring device 1110 is positioned within the hatband 1105 of a cap 1107. As illustrated, the alarm device 1121 is separated from the monitoring device 1110 and is present on underside of the brim 1009 of the cap 1107 such that the alarm device 1121 is within the user's field of vision. Finally, FIG. 12 illustrates an eyewear monitoring system 1201 in which a monitoring device 1210 is incorporated into the brow bar 1203, and/or temple bar 1205 of pair of safety glasses 1207. In one embodiment of such an eyewear system 1201, the alert device may include the display 1213 of an alert message on the lens 1209 of the glasses 1207.

The present invention has been described in general and in detail by way of examples. Persons of skill in the art understand that the invention is not limited to the specific embodiments disclosed. Modification and variations of the general concept may be made without departing from the scope of the invention as defined by the following claims or equivalents, including, equivalent components.

We claim:

1. A method for continuous non-invasive monitoring of thermal stress of a user, the method comprising the steps of:

a) providing a device comprising,
      at least one first temperature sensor configured to be placed in thermal contact with skin of the user,
      at least one second temperature sensor, and
      an insulating layer positioned between the first and second temperature sensor,
      where the insulating layer comprises an outer periphery and a thermal conductance ($L_{band}$),
      where the thermal conductance ($L_{band}$) of the insulating layer satisfies the following equation $$\sqrt{1 + \frac{2L_{band}^2}{L_{core}^2} + \frac{2L_{band}}{L_{core}}} \leq 10$$

where $L_{core}$ is between 36 and 140 W/m²K, and
   where the temperature sensors are located at least a distance (w) from a peripheral edge of the insulating layer, where the distance (w) satisfies the following equation $$w = \frac{0.0436 D_{core}\sqrt{72090 + 1101 Q_{evap} + 118 Q_{evap} L_{band}}}{\sqrt{L_{band}}}$$

where $Q_{evap}$ is 250 W/m² or less, and
   where $D_{core}$ is between 0.002 and 0.005 meters b) placing said device in thermal contact with the skin of the user;
   c) determining heat flux from the skin through the device at known time intervals; and
   d) determining core temperature and change in core temperature as a function of heat flux.

2. The method of claim 1, further comprising the subsequent step of comparing the determined core temperature to a threshold temperature range.

3. The method of claim 2, further comprising the subsequent step of providing an alert when the determined core temperature is outside the threshold temperature range.

4. The method of claim 1, further comprising the subsequent step of comparing the determined change in core temperature to a threshold temperature change range.

5. The method of claim 4, further comprising the subsequent step of providing an alert when the determined change in core temperature is outside the threshold temperature range.

6. The method of claim 5, where the alert is provided to the user.

7. The method of claim 6, where the alert is selected from a group consisting of audible alert, visual display, vibration, and a combination thereof.

8. The method of claim 1, where the step of placing said device in contact with the skin of the user comprises placing said device in contact with the skin of the user proximate to a temporal artery of the user.

9. The method of claim 1, where the step of placing said device in contact with the skin of the user comprises affixing said device to the skin of the user.

10. The method of claim 1, where the thermal conductance ($L_{band}$) of the insulating layer is between 230 and 910 W/m² K, and where the distance (w) is between 3.5 cm and 7 cm.

11. A device for continuous non-invasive monitoring thermal stress of a user, the device comprising:
   at least one first temperature sensor configured to be placed in thermal contact with skin of the user,
   at least one second temperature sensor, and
   an insulating layer positioned between the first and second temperature sensor,
   where the insulating layer comprises an outer periphery and a thermal conductance ($L_{band}$),
   where the thermal conductance ($L_{band}$) of the insulating layer satisfies the following equation $$\sqrt{1 + \frac{2L_{band}^2}{L_{core}^2} + \frac{2L_{band}}{L_{core}}} \leq 10$$

where $L_{core}$ is between 36 and 140 W/m²K, and
   where the temperature sensors are located at least a distance (w) from a peripheral edge of the insulating layer, where the distance (w) satisfies the following equation $$w = \frac{0.0436 D_{core}\sqrt{72090 + 1101 Q_{evap} + 118 Q_{evap} L_{band}}}{\sqrt{L_{band}}}$$

where $Q_{evap}$ is 250 W/m² or less, and
where $D_{core}$ is between 0.002 and 0.005 meters.

12. The device of claim 11, further comprising a processor, where the processor is configured to receive input from each of the first and second temperature sensors and determine a core temperature.

13. The device of claim 12, where the processor is configured to compare the determined core temperature to a stored threshold core temperature range, and where the processor is configured to output an alert signal when the determined core temperature is outside the stored threshold core temperature range.

14. The device of claim 12, where the processor is configured to determine a change in core temperature.

15. The device of claim 14, where the processor is configured to compare the determined change in core temperature to a stored threshold change in core temperature range, and where the processor is configured to output an alert signal when the determined change in core temperature is outside the stored threshold change in core temperature range.

16. The device of claim 15, where the processor is configured to compare the determined core temperature to a stored warning core temperature range and output a warning alert signal when the determined core temperature is outside the stored warning core temperature range, and where the processor is configured to compare the determined change in core temperature to a stored warning change in core temperature range, and where the processor is configured to output a warning alert signal when the determined change in core temperature is outside the stored warning change in core temperature range.

17. The device of claim 11, further comprising an alert mechanism.

18. The device of claim 11, further comprising a backing and an adhesive present on said backing, where the backing and adhesive are configured to affix the device to the skin of the user.

19. A system for continuous monitoring of thermal stress of a user, the system comprising,
a thermal stress monitoring device; and
a garment;
where the garment is configured to place the monitoring device in thermal communication with skin of the user, and where the monitoring device comprises,
at least one first temperature sensor configured to be placed in thermal contact with skin of the user,
at least one second temperature sensor, and
an insulating layer positioned between the first and second temperature sensor,
where the insulating layer comprises an outer periphery and a thermal conductance ($L_{band}$),
where the thermal conductance ($L_{band}$) of the insulating layer satisfies the following equation $$\sqrt{1 + \frac{2L_{band}^2}{L_{core}^2} + \frac{2L_{band}}{L_{core}}} \leq 10$$

where $L_{core}$ is between 36 and 140 W/m²K, and
where the temperature sensors are located at least a distance (w) from a peripheral edge of the insulating layer, where the distance (w) satisfies the following equation $$w = \frac{0.0436 D_{core}\sqrt{72090 + 1101 Q_{evap} + 118 Q_{evap} L_{band}}}{\sqrt{L_{band}}}$$

where $Q_{evap}$ is 250 W/m² or less, and
where $D_{core}$ is between 0.002 and 0.005 meters.

20. The system of claim 19, further comprising an alert mechanism.

21. The system of claim 20, where the alert mechanism is included in the garment.

22. The system of claim 20, where the alert mechanism is configured such that an alert generated by the alert mechanism may not be reset by user being monitored.

23. The system of claim 19, where the garment is selected from the group consisting of a bandage, a sweatband, a hardhat, a welding helmet, a hood, eyewear, and a cap.

24. The system of claim 19, further comprising a proximity sensor configured to determine if the monitoring device is in contact with the user, and where the system is configured to output an alert signal if the device is not in contact with the user.

* * * * *